(12) United States Patent
Frey et al.

(10) Patent No.: US 10,577,291 B2
(45) Date of Patent: Mar. 3, 2020

(54) METHODS FOR PRODUCING JET-RANGE HYDROCARBONS

(71) Applicant: UOP LLC, Des Plaines, IL (US)

(72) Inventors: Stanley Joseph Frey, Palatine, IL (US); Geoffrey William Fichtl, Chicago, IL (US); Paul Barger, Arlington Heights, IL (US); Scott M. Roney, Wheaton, IL (US); Steven Lee Krupa, Fox River Grove, IL (US); Christopher P. Nicholas, Evanston, IL (US)

(73) Assignee: UOP LLC, Des Plaines, IL (US)

( * ) Notice: Subject to any disclaimer, the term of this patent is extended or adjusted under 35 U.S.C. 154(b) by 126 days.

(21) Appl. No.: 14/073,058

(22) Filed: Nov. 6, 2013

(65) Prior Publication Data

US 2015/0045599 A1    Feb. 12, 2015

Related U.S. Application Data

(60) Provisional application No. 61/725,398, filed on Nov. 12, 2012.

(51) Int. Cl.
*C07C 2/08*    (2006.01)
*C07C 5/03*    (2006.01)
(Continued)

(52) U.S. Cl.
CPC .............. *C07C 2/12* (2013.01); *B01J 29/40* (2013.01); *B01J 29/7034* (2013.01); *B01J 29/7042* (2013.01); *B01J 29/7046* (2013.01); *C07C 5/03* (2013.01); *C10G 50/00* (2013.01); *B01J 29/7038* (2013.01); *C07C 2529/89* (2013.01); *C10G 2300/301* (2013.01); *C10G 2300/4081* (2013.01); *C10G 2400/08* (2013.01); *C10G 2400/20* (2013.01); *C10G 2400/22* (2013.01)

(58) Field of Classification Search
CPC ..................................... C07C 2/12; C07C 5/03
USPC ..... 585/255, 517, 533, 502, 500; 502/60, 64
See application file for complete search history.

(56) References Cited

U.S. PATENT DOCUMENTS 3,832,418 A * 8/1974 Bercik .................... B01J 23/74
                                                        502/219
5,510,306 A * 4/1996 Murray ................... B01J 29/65
                                                        502/64
(Continued)

FOREIGN PATENT DOCUMENTS

WO      2011140560 A1    11/2011
WO   WO 2011140560 A1 * 11/2011 ............... C10G 3/42

*Primary Examiner* — Philip Y Louie
(74) *Attorney, Agent, or Firm* — Paschall & Associates, LLC; James C. Paschall

(57) ABSTRACT

A method for producing jet-range hydrocarbons includes passing a stream comprising renewable $C_4$ olefins to an oligomerization reactor containing a zeolite catalyst to produce an oligomerized effluent, separating the oligomerized effluent to produce a jet range hydrocarbon stream and a recycle stream comprising $C_8$ olefins, and passing at least a portion of the recycle stream to the oligomerization reactor. A first at least about 10% of the jet-range hydrocarbon stream hydrocarbons boil between n-octane and n-undecane and wherein a second at least about 10% of the jet-range hydrocarbon stream hydrocarbons boil between n-dodecane and n-pentadecane.

12 Claims, 2 Drawing Sheets

(51) Int. Cl.
    *C07C 2/12*         (2006.01)
    *C10G 50/00*     (2006.01)
    *B01J 29/40*      (2006.01)
    *B01J 29/70*      (2006.01)

(56) References Cited

U.S. PATENT DOCUMENTS

| Patent/Publication No. | | Date | Inventor | Classification |
|---|---|---|---|---|
| 5,608,133 | A * | 3/1997 | Chang | B01J 21/06 585/502 |
| 6,548,040 | B1 * | 4/2003 | Rouleau | B01J 20/18 208/134 |
| 6,689,927 | B1 * | 2/2004 | Frame | C07C 2/08 585/510 |
| 7,268,268 | B2 * | 9/2007 | al-Soufi | C07C 2/12 585/510 |
| 7,786,337 | B2 | 8/2010 | Brown et al. | |
| 8,585,410 | B2 | 11/2013 | Nicholas et al. | |
| 2003/0158272 | A1 * | 8/2003 | Davis | B01J 23/78 518/719 |
| 2006/0199987 | A1 * | 9/2006 | Kuechler | C07C 2/12 585/502 |
| 2007/0173676 | A1 * | 7/2007 | Brown | C07C 2/18 585/533 |
| 2011/0288352 | A1 * | 11/2011 | Peters | C10G 3/42 585/14 |
| 2012/0078022 | A1 * | 3/2012 | Kimura | B01J 27/182 585/16 |

* cited by examiner

METHODS FOR PRODUCING JET-RANGE HYDROCARBONS

CROSS-REFERENCE TO RELATED APPLICATIONS

This application claims the benefit of priority to United State provisional application Ser. No. 61/725,398, filed Nov. 12, 2012, the contents of which are herein incorporated by reference in their entirety.

FIELD OF THE INVENTION

The present disclosure generally relates to methods for producing renewable fuels and chemicals from biorenewable sources and the renewable fuels and chemicals produced thereby, and more particularly relates to methods for producing jet-range hydrocarbons from alkanols, including for example isobutanol, and the jet-range hydrocarbons produced thereby.

DESCRIPTION OF RELATED ART

As the worldwide demand for fuel increases, interest in sources other than crude oil from which to produce transportation fuels, including aviation fuels, is ever increasing. For example, due to the growing environmental concerns over fossil fuel extraction and economic concerns over exhausting fossil fuel deposits, there is a demand for using an alternate or "green" feed source for producing hydrocarbons for use as transportation fuels and for use in other industries. Such sources of interest include, for example, biorenewable sources, such as vegetable and seed oils, animal fats, and algae byproducts, among others as are well-known to those skilled in the art. A conventional catalytic hydro-processing technique is known for converting a biorenewable feedstock into green diesel fuel that may be used as a substitute for the diesel fuel produced from crude oil. As used herein, the terms "green diesel fuel" and "green jet fuel" refer to fuel produced from biorenewable sources, in contrast to those produced from crude oil. The process also supports the possible co-production of propane and other light hydrocarbons, as well as naphtha or green jet fuel.

Acceptance of fuels produced from biorenewable sources in the aviation industry has, to date, been slower than desirable. In some instances, the fatty acids from vegetable and seed oils used in the conventional catalytic hydro-processing techniques noted above may have several specific disadvantages compared to petroleum-derived fuels. For aviation engines, such as gas turbine engines, the cold flow properties of the long-chain fatty esters from vegetable and seed oils may, in some instances, be sufficiently poor so as to cause operational problems, even when used at levels in the fuel as low as about 5% by weight. Under cold conditions, the precipitation and crystallization of fatty paraffin waxes has the potential to cause flow and filter plugging problems. Further, the high temperature instability of, for example, the esters and olefinic bonds in vegetable and seed oils is also a potential problem.

To avoid the problems that are sometimes encountered in using biorenewable fatty acids and the like as the feedstock for the production of green fuels, alternative production schemes using isoalkanols, such as for example isobutanol, as feedstocks have been proposed. Renewable isoalkanols are typically formed by fermentation. For example, the feedstock for the fermentation process can be any suitable fermentable feedstock known in the art, such as sugars derived from agricultural crops including sugarcane, corn, etc. Alternatively, the fermentable feedstock can be prepared by the hydrolysis of biomass, for example lignocellulosic biomass (e.g. wood, corn stover, switchgrass, herbiage plants, ocean biomass, etc.). In order to produce jet-range fuels from isoalkanols, in one example known in the art, isobutanol is first dehydrated to form butenes. The butenes are then oligomerized to preferentially form trimers, tetramers, and sometimes pentamers of isobutene, i.e. $C_{12}$, $C_{16}$, and sometimes $C_{20}$ olefins. Finally, the olefins are hydrogenated to form $C_{12}$, $C_{16}$, and $C_{20}$ paraffins.

This sequence of processing steps, however, results in a product with a boiling point distribution that has well-defined boiling point steps corresponding to only a few isomers of the $C_{12}$, $C_{16}$, and $C_{20}$ paraffins, which does not resemble regular petroleum-derived jet fuel. The stepping character of the boiling point distribution reflects the tri-component nature of this hydrocarbon mixture, as the intermediate olefin products that are used to make paraffins are simple additive oligomers that have a carbon number that is a multiple of four. Such a stepped boiling point distribution is different from traditional petroleum-derived jet fuel, and has been met with some skepticism in the aviation industry.

Accordingly, it is desirable to provide jet-range fuels and methods for producing jet-range fuels from a biorenewable feedstock that does not include fatty acids or esters. Further, it is desirable to provide jet-range fuels and methods for producing jet-range fuels from such feed stocks that have a boiling point distribution that more closely resembles petroleum-derived jet-range fuels. Further still, other desirable features and characteristics of the present disclosure will become apparent from the subsequent detailed description and the appended claims, when taken in conjunction with the accompanying drawing and this background.

SUMMARY OF THE INVENTION

Methods for producing jet-range hydrocarbons and the jet-range hydrocarbons produced thereby are disclosed herein. While these methods find greatest utility in converting feedstocks from alcohols allowing for production of jet fuels from renewable sources, this is not intended to limit the application of the method. The methods can also find utility with conversion of $C_4$ olefins to jet fuel with feedstocks that are derived from petroleum. The methods are suitable to produce jet-range hydrocarbons that exhibit smooth boiling point characteristics.

In an exemplary embodiment, a method for producing jet-range hydrocarbons includes passing a stream comprising $C_4$ olefins to an oligomerization reactor comprising a zeolite catalyst to produce an oligomerized effluent, wherein a first at least about 10% of the oligomerized effluent hydrocarbons boil between n-octane and n-undecane and wherein a second at least about 10% of the oligomerized effluent hydrocarbons boil between n-dodecane and n-pentadecane, separating the oligomerized product by distillation to produce a jet range hydrocarbon stream and a recycle stream comprising $C_8$ olefins, and passing at least a portion of the recycle stream to the oligomerization reactor.

In another embodiment, a method for producing jet-range hydrocarbons includes passing a stream comprising $C_4$ olefins to an oligomerization reactor containing a zeolite catalyst to produce an oligomerized effluent. At least about 10% of the oligomerized product jet-range hydrocarbons boil between n-octane and n-undecane and another at least 10% of the oligomerized product jet-range hydrocarbons boil between n-dodecane and n-pentadecane. The method further includes separating the oligomerized product by distillation to produce a jet range hydrocarbon stream and a recycle stream including $C_8$ olefins and passing at least a portion of the recycle stream to the reactor.

In yet another embodiment, a method for producing jet-range hydrocarbons includes passing a stream comprising $C_4$ olefins to an oligomerization reactor comprising a zeolite catalyst to produce an oligomerized effluent, wherein a first at least about 10% of the oligomerized effluent hydrocarbons boil between n-octane and n-undecane and wherein a second at least about 10% of the oligomerized effluent hydrocarbons boil between n-dodecane and n-pentadecane, separating the oligomerized product by distillation to produce a jet range hydrocarbon stream and a recycle stream comprising $C_8$ olefins, dimerizing the $C_4$ olefins over SPA or acidic ion exchange resin catalysts, wherein conversion of $C_4$ olefins in the dimerizing step is greater than or equal to about 90%, and passing at least a portion of the recycle stream to the oligomerization reactor. Dimerizing the $C_4$ olefins is performed prior to passing the $C_4$ olefin oligomers to the oligomerization reactor.

This summary is provided to introduce a selection of concepts in a broad and simplified form that are further described below in the detailed description. This summary is not intended to identify or delineate key features or essential features of the claimed subject matter, nor is it intended to be used as an aid in determining the scope of the claimed subject matter.

BRIEF DESCRIPTION OF THE DRAWINGS

Exemplary embodiments of the present disclosure will hereinafter be described in conjunction with the following drawing figures, wherein like numerals denote like elements, and wherein.

DEFINITIONS

Figure 1:
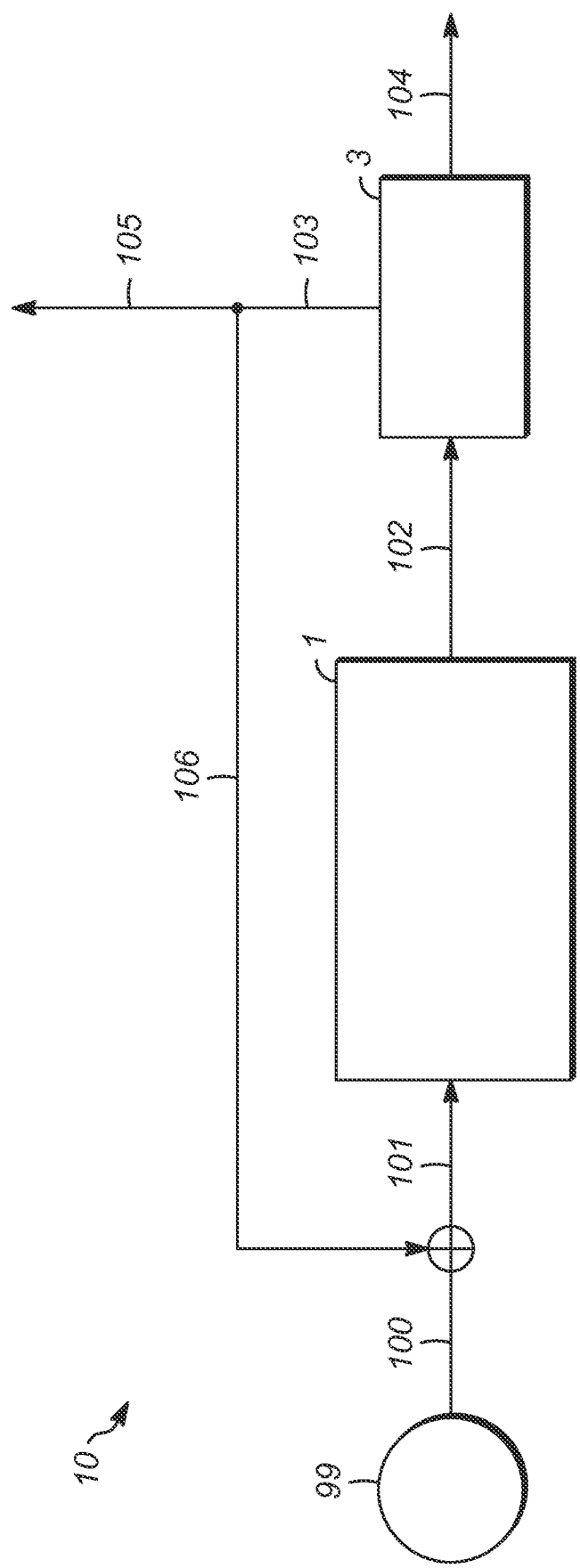
FIG. 1 schematically illustrates an exemplary embodiment of a system utilizing a process for producing jet-range hydrocarbons from biorenewable feedstocks.

As used herein, the term "stream" can include various hydrocarbon molecules and other substances. Moreover, the term "stream comprising Cx hydrocarbons" or "stream comprising Cx olefins" can include a stream comprising hydrocarbon or olefin molecules, respectively, with "x" number of carbon atoms, suitably a stream with a majority of hydrocarbons or olefins, respectively, with "x" number of carbon atoms and preferably a stream with at least 75 wt-% hydrocarbons or olefin molecules, respectively, with "x" number of carbon atoms. Moreover, the term "stream comprising Cx+ hydrocarbons" or "stream comprising Cx+ olefins" can include a stream comprising a majority of hydrocarbon or olefin molecules, respectively, with more than or equal to "x" carbon atoms and suitably less than 10 wt-% and preferably less than 1 wt-% hydrocarbon or olefin molecules, respectively, with x−1 carbon atoms. Lastly, the term "Cx− stream" can include a stream comprising a majority of hydrocarbon or olefin molecules, respectively, with less than or equal to "x" carbon atoms and suitably less than 10 wt-% and preferably less than 1 wt-% hydrocarbon or olefin molecules, respectively, with x+1 carbon atoms.

As used herein, the term "zone" can refer to an area including one or more equipment items and/or one or more sub-zones. Equipment items can include one or more reactors or reactor vessels, heaters, exchangers, pipes, pumps, compressors, controllers and columns. Additionally, an equipment item, such as a reactor, dryer, or vessel, can further include one or more zones or sub-zones.

As used herein, the term "substantially" can mean an amount of at least generally about 70%, preferably about 80%, and optimally about 90%, by weight, of a compound or class of compounds in a stream.

As used herein, the term "gasoline" can include hydrocarbons having a boiling point temperature in the range of about 25 to about 200° C. and at about atmospheric pressure.

As used herein, the term "diesel" can include hydrocarbons having a boiling point temperature in the range of about 150 to about 400° C. and preferably about 200 to about 400° C.

As used herein, the term "vapor" can mean a gas or a dispersion that may include or consist of one or more hydrocarbons.

As used herein, the term "overhead stream" can mean a stream withdrawn at or near a top of a vessel, such as a column.

As used herein, the term "bottom stream" can mean a stream withdrawn at or near a bottom of a vessel, such as a column.

As depicted, process flow lines in the figures can be referred to interchangeably as, e.g., lines, pipes, feeds, gases, products, discharges, parts, portions, or streams.

As used herein, "bypassing" with respect to a vessel or zone means that a stream does not pass through the zone or vessel bypassed although it may pass through a vessel or zone that is not designated as bypassed.

The term "communication" means that material flow is operatively permitted between enumerated components.

The term "downstream communication" means that at least a portion of material flowing to the subject in downstream communication may operatively flow from the object with which it communicates.

The term "upstream communication" means that at least a portion of the material flowing from the subject in upstream communication may operatively flow to the object with which it communicates.

The term "direct communication" means that flow from the upstream component enters the downstream component without undergoing a compositional change due to physical fractionation or chemical conversion.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottom stream back to the bottom of the column. Feeds to the columns may be preheated. The top pressure is the pressure of the overhead vapor at the outlet of the column. The bottom temperature is the liquid bottom outlet temperature. Overhead lines and bottom lines refer to the net lines from the column downstream of the reflux or reboil to the column.

As used herein, the term "boiling point temperature" means atmospheric equivalent boiling point (AEBP) as calculated from the observed boiling temperature and the distillation pressure, as calculated using the equations furnished in ASTM D1160 appendix A7 entitled "Practice for Converting Observed Vapor Temperatures to Atmospheric Equivalent Temperatures".

As used herein, "taking a stream from" means that some or all of the original stream is taken.

Furthermore, as used in the present disclosure, the terms "renewably-based" or "renewable" denote that the carbon content of the renewable alcohol (and olefin, di-olefin, etc., or subsequent products prepared from renewable alcohols, olefins, di-olefins, etc. as described herein), is from a "new carbon" source as measured by ASTM test method D6866-05, "Determining the Bio-based Content of Natural Range Materials Using Radiocarbon and Isotope Ratio Mass Spectrometry Analysis", incorporated herein by reference in its entirety. This test method measures the $^{14}C/^{12}C$ isotope ratio in a sample and compares it to the $^{14}C/^{12}C$ isotope ratio in a standard 100% bio-based material to give percent bio-based content of the sample. Additionally, "Bio-based materials" are organic materials in which the carbon comes from recently (on the order of centuries) fixated $CO_2$ present in the atmosphere using sunlight energy (photosynthesis). On land, this $CO_2$ is captured or fixated by plant life (e.g., agricultural crops or forestry materials). In the oceans, the $CO_2$ is captured or fixated by photosynthesizing bacteria or phytoplankton. For example, a bio-based material has a $^{14}C/^{12}C$ isotope ratio greater than 0. Contrarily, a fossil-based material has a $^{14}C/^{12}C$ isotope ratio of about 0. The term "renewable" with regard to compounds such as alcohols or hydrocarbons (olefins, di-olefins, polymers, etc.) also refers to compounds prepared from biomass using thermochemical methods (e.g., Fischer-Tropsch catalysts), biocatalysts (e.g., fermentation), or other processes, for example as described herein.

A small amount of the carbon atoms in the carbon dioxide in the atmosphere is the radioactive isotope $^{14}C$. This $^{14}C$ carbon dioxide is created when atmospheric nitrogen is struck by a cosmic ray generated neutron, causing the nitrogen to lose a proton and form carbon of atomic mass 14 ($^{14}C$), which is then immediately oxidized, to carbon dioxide. A small but measurable fraction of atmospheric carbon is present in the form of $^{14}C$. Atmospheric carbon dioxide is processed by green plants to make organic molecules during the process known as photosynthesis. Virtually all forms of life on Earth depend on this green plant production of organic molecules to produce the chemical energy that facilitates growth and reproduction. Therefore, the $^{14}C$ that forms in the atmosphere eventually becomes part of all life forms and their biological products, enriching biomass and organisms which feed on biomass with $^{14}C$. In contrast, carbon from fossil fuels does not have the signature $^{14}C/^{12}C$ ratio of renewable organic molecules derived from atmospheric carbon dioxide. Furthermore, renewable organic molecules that biodegrade to $CO_2$ do not contribute to an increase in atmospheric greenhouse gases as there is no net increase of carbon emitted to the atmosphere.

Assessment of the renewably based carbon content of a material can be performed through standard test methods, e.g. using radiocarbon and isotope ratio mass spectrometry analysis. ASTM International (formally known as the American Society for Testing and Materials) has established a standard method for assessing the bio-based content of materials. The ASTM method is designated ASTM-D6866.

The application of ASTM-D6866 to derive "biobased content" is built on the same concepts as radiocarbon dating, but without use of the age equations. The analysis is performed by deriving a ratio of the amount of radiocarbon ($^{14}C$) in an unknown sample compared to that of a modern reference standard. This ratio is reported as a percentage with the units "pMC" (percent modern carbon). If the material being analyzed is a mixture of present day radiocarbon and fossil carbon (containing very low levels of radiocarbon), then the pMC value obtained correlates directly to the amount of biomass material present in the sample.

DETAILED DESCRIPTION

The following detailed description is merely exemplary in nature and is not intended to limit the invention or the application and uses of the invention. As used herein, the word "exemplary" means "serving as an example, instance, or illustration." Any embodiment described herein as "exemplary" is not necessarily to be construed as preferred or as advantageous over other embodiments. Furthermore, there is no intention to be bound by any theory presented in the preceding background or the following detailed description.

Disclosed herein are embodiments of a method for producing jet-range hydrocarbons from $C_4$ olefins via oligomerization, and the jet-range hydrocarbons produced thereby. As used herein, the term "jet-range hydrocarbons" or "jet-range paraffins" refers to a composition of hydrocarbons that boil in a range such that the volatility characteristics of the hydrocarbon (or paraffinic form of the hydrocarbon after hydrogenation) that substantially conform to the volatility standards of flash point and distillation range set forth in ASTM D7566-11a, "Standard Specification for Aviation Turbine Fuel Containing Synthesized Hydrocarbons," promulgated by ASTM International, Inc. of West Conshohoken, Pa. The jet-range hydrocarbons produced by the exemplary methods described herein do not suffer from the cold flow operating problems that are sometimes encountered by jet-range hydrocarbons derived from renewable sources including fatty acids and esters, such as precipitation and crystallization of paraffin waxes. Further, the jet-range hydrocarbons produced by the exemplary methods described herein do not suffer from the well-defined boiling point steps observed in other alcohol-derived jet-range hydrocarbons because of the use of a novel hydrocarbon oligomerization technique, as will be described in greater detail below. As such, the jet-range hydrocarbons produced by the exemplary methods described herein result in a relatively smooth boiling point distribution that more closely resembles petroleum-derived jet-range fuels, as compared with the renewable source-derived jet-range hydrocarbons known in the art, as described above. In this manner, the jet-range hydrocarbons produced by the exemplary methods are anticipated to find greater acceptance and use in the aviation industry, thus reducing reliance on petroleum-based sources.

Reference will hereafter be made to FIG. 1, which schematically illustrates an exemplary system 10 utilizing an exemplary method for producing jet-range hydrocarbons from a mixture of olefins that includes at least $C_4$ olefins. System 10 includes a feedstock source 99, i.e., a source of olefins that includes at least the $C_4$ olefins. In an embodiment, the feedstock source 99 includes butenes, for example butenes derived from a biorenewable source. The renewable butenes can be derived from their corresponding alcohols (i.e., $C_4$ alcohols, especially including isobutanol), which are typically formed by fermentation or by condensation reactions of synthesis gas. For example, the feedstock for the fermentation process can be any suitable fermentable feedstock known in the art, such as sugars derived from agricultural crops including sugarcane, corn, etc. Alternatively, the fermentable feedstock can be prepared by the hydrolysis of biomass, for example lignocellulosic biomass (e.g. wood, corn stover, switchgrass, herbiage plants, ocean biomass, etc.). In another example, renewable alcohols, such as isobutanols, can be prepared photosynthetically, for example using cyanobacteria or algae engineered to produce isobutanol and/or other alcohols. When produced photosynthetically, the feedstock for producing the resulting renewable alcohols is light, water, and $CO_2$, which is provided to the photosynthetic organism (e.g., cyanobacteria or algae). Additionally, other known methods, whether biorenewable or otherwise, for producing isobutanol are suitable for supplying the feedstock source 99; the methods described herein are not intended to be limited by the use of any particular renewable feed source.

The $C_4$ olefins (derived and converted from the $C_4$ alcohols) from the feedstock source 99 are mixed with stream 106, which includes $C_8$-hydrocarbons, and are delivered via streams 100, 101 to an oligomerization reactor 1. In the oligomerization reactor 1, at least a portion of the $C_4$ olefins are converted into a mixture of heavier boiling hydrocarbons including jet range hydrocarbons via oligomerization by reacting the $C_4$ olefins using a zeolitic oligomerization catalyst. Under appropriate conditions zeolitic catalysts such as MTT, TON, MFI, and MTW will yield jet-range hydrocarbons with a broader distribution of components than do non-zeolitic catalysts, such as sulfonated polystyrene resins or solid phosphoric acid catalysts. The increase in the distribution and variety of carbon numbers made by using zeolitic catalysts as compared to a non-zeolitic catalyst is shown in Table 1, below.

TABLE 1

| Plant/Run | 2B-310C/592 | | | | | | | 2B-310C/593 | |
|---|---|---|---|---|---|---|---|---|---|
| Catalyst | 32964-58 80% MTW/20% Clay | | | | | | | 33926-89CB 80% MTT/20% Al2O3 | |
| HOS | 60-70 | 115-125 | 140-150 | 165-175 | 195-200 | 245-250 | 260-265 | 55-65 | 85-95 |
| Feed | 10% C4 = s/C5s/20% C8 = s/160 ppm TBA | | | | C5s/40% C8 = s | | | iC5/40% C8 = s | |
| LHSV (hr-1) | 0.56 | 0.75 | 0.75 | 0.75 | 0.75 | 0.75 | 0.75 | 0.75 | |
| Bed Temp (° C.) | 111 | 112 | 131 | 150 | 170 | 170 | 179 | 172 | |
| Pressure (psig) | | | | 990 | | | | 890 | 710 |
| Conversions (%) | | | | | | | | | |
| iC4= | 99 | 99 | 99 | 99 | 99 | — | — | — | — |
| nC4 = s | 89 | 84 | 93 | 93 | 94 | — | — | — | — |
| Total C4 = s | 98 | 97 | 98 | 98 | 99 | — | — | — | — |
| C8s | 29 | 24 | 40 | 67 | 83 | 88.0 | 85.3 | 89 | 88.3 | 82.8 |
| Selectivities (wt %) | | | | | | | | | |
| C3 (wtppm) | 0 | 0 | 1 | 17 | 36 | 27 | 0 | 42 | 30 | 29 |
| iC4 | 0.4 | 0.3 | 1.0 | 1.9 | 3.1 | 2.1 | 0.4 | 2.4 | 1.6 | 1.6 |
| C4 = s | — | — | — | — | — | 0.4 | 3.3 | 0.5 | 0.6 | 0.6 |
| C6-7 | 3 | 3 | 4 | 4 | 5 | 4 | 3 | 4 | 5 | 5 |
| C8s | — | — | — | — | — | — | — | — | — | — |
| C9-11 | 5 | 4 | 10 | 14 | 14 | 13 | 5 | 13 | 14 | 13 |
| C12 | 66 | 67 | 58 | 42 | 31 | 33 | 66 | 30 | 39 | 40 |
| C13-15 | 6 | 4 | 10 | 17 | 22 | 21 | 6 | 22 | 19 | 19 |
| C16 | 19 | 20 | 15 | 16 | 18 | 19 | 19 | 19 | 16 | 15 |
| C17-19 | 0.3 | 0.2 | 0.5 | 1.7 | 3.5 | 3.4 | 0.3 | 3.9 | 2.1 | 2.0 |
| C20 | 0.9 | 0.8 | 1.3 | 3.4 | 4.1 | 5.0 | 0.9 | 4.8 | 3.3 | 3.2 |
| C20+ | 0.0 | 0.0 | 0.0 | 0.1 | 0.2 | 0.3 | 0.0 | 0.4 | 0 | 0.1 |
| Deactivation Rate (Δ % Conwhr) | | | | | | -0.05 | | -0 | | -0.02 |

| Plant/Run | 2B-310C/593 | | | | 2B-310C/594 | | | 2B-310C/591 |
|---|---|---|---|---|---|---|---|---|
| Catalyst | 33926-89CB 80% MTT/20% Al2O3 | | | | 34222-1 75% MFI-23/Al2O3 | | | Amberlyst 36 |
| HOS | 140-150 | 168-173 | 180-190 | 205-215 | 30-40 | 85-95 | 125-135 | 1375-1385 |
| Feed | iC5/40% C8 = s | | | | iC5/40% C8 = s | | | C4 = /C5/C8 = TBA |
| LHSV (hr-1) | 1.50 | 1.50 | 1.50 | 0.75 | | 0.75 | | 0.75 |
| Bed Temp (° C.) | 171 | 187 | 197 | 172 | | 172 | 192 | 112 |
| Pressure (psig) | 870 | 815 | | | | 1000 | | 990 |
| Conversions (%) | | | | | | | | |
| iC4= | — | — | — | — | — | — | — | 99 |
| nC4 = s | — | — | — | — | — | — | — | 65 |

TABLE 1-continued

|  | | | | | | | | |
|---|---|---|---|---|---|---|---|---|
| Total C4=s | — | — | — | — | — | — | — | 97 |
| C8s Selectivities (wt %) | 70 | 74 | 80 | 75 | 88.8 | 81.6 | 91 | 43 |
| C3 (wtppm) | 25 | 37 | 65 | 23 | 131 | 100 | 300 | |
| iC4 | 1.0 | 1.4 | 2.5 | 1.2 | 1.2 | 1.0 | 1.2 | |
| C4=s | 1.1 | 1.0 | 1.0 | 0.8 | 0.2 | 0.4 | 0.2 | |
| C6-7 | 4 | 5 | 7 | 5 | 3 | 3 | 3 | 1 |
| C8s | — | — | — | — | — | — | — | — |
| C9-11 | 11 | 13 | 16 | 12 | 9 | 10 | 9 | 3 |
| C12 | 53 | 45 | 36 | 47 | 27 | 34 | 21 | 71 |
| C13-15 | 14 | 16 | 19 | 16 | 20 | 19 | 21 | 4 |
| C16 | 14 | 14 | 15 | 15 | 21 | 20 | 20 | 20 |
| C17-19 | 0.7 | 1.2 | 2.1 | 1.3 | 5.3 | 3.8 | 6.7 | 0.1 |
| C20 | 2.1 | 2.4 | 2.5 | 2.7 | 7.7 | 5.9 | 9.2 | 0.4 |
| C20+ | 0.0 | 0.0 | 0.1 | 0.0 | 5.3 | 2.4 | 9.0 | 0.0 |
| Deactivation Rate (Δ % Conv/hr) | −0.10 | (−0.27) | −0.08 | −0.37 | | −0.13 | −0.10 | |

The carbon numbers shown in Table 1 are not necessarily actual carbon numbers, but rather reference points based on boiling points of known GCMS and GC peaks. For example, it is conceivable that a very isomerized $C_{16}$ olefin could be counted in the "$C_{13}$-$C_{15}$" block in this Table, due to the strong boiling point suppression that occurs with isomerization.

As noted, the oligomerization catalyst may include a zeolitic catalyst. The zeolite may comprise between about 5 and about 95 wt % of the catalyst, for example between about 5 and about 85 wt %. Suitable zeolites include zeolites having a structure from one of the following classes: MFI, MEL, ITH, IMF, TUN, FER, BEA, FAU, BPH, MEI, MSE, MWW, UZM-8, MOR, OFF, MTW, TON, MTT, AFO, ATO, and AEL. 3-letter codes indicating a zeotype are as defined by the Structure Commission of the International Zeolite Association and are maintained at http://www.iza-structure.org/databases. UZM-8 is as described in U.S. Pat. No. 6,756,030. In a preferred aspect, the oligomerization catalyst may comprise a zeolite with a framework having a ten-ring pore structure. Examples of suitable zeolites having a ten-ring pore structure include TON, MTT, MFI, MEL, AFO, AEL, EUO and FER. In a further preferred aspect, the oligomerization catalyst comprising a zeolite having a ten-ring pore structure may comprise a uni-dimensional pore structure. A uni-dimensional pore structure indicates zeolites containing non-intersecting pores that are substantially parallel to one of the axes of the crystal. The pores preferably extend through the zeolite crystal. Suitable examples of zeolites having a ten-ring uni-dimensional pore structure may include MTT. In a further aspect, the oligomerization catalyst comprises an MTT zeolite.

The oligomerization catalyst may be formed by combining the zeolite with a binder, and then forming the catalyst into pellets. The pellets may optionally be treated with a phosphorus reagent to create a zeolite having a phosphorous component between 0.5 and 15 wt % of the treated catalyst. The binder is used to confer hardness and strength on the catalyst. Binders include alumina, aluminum phosphate, silica, silica-alumina, zirconia, titania and combinations of these metal oxides, and other refractory oxides, and clays such as montmorillonite, kaolin, palygorskite, smectite and attapulgite. A preferred binder is an aluminum-based binder, such as alumina, aluminum phosphate, silica-alumina and clays.

One of the components of the catalyst binder utilized in the present invention is alumina. The alumina source may be any of the various hydrous aluminum oxides or alumina gels such as alpha-alumina monohydrate of the boehmite or pseudo-boehmite structure, alpha-alumina trihydrate of the gibbsite structure, beta-alumina trihydrate of the bayerite structure, and the like. A suitable alumina is available from UOP LLC under the trademark Versal. A preferred alumina is available from Sasol North America Alumina Product Group under the trademark Catapal. This material is an extremely high purity alpha-alumina monohydrate (pseudo-boehmite) which after calcination at a high temperature has been shown to yield a high purity gamma-alumina.

A suitable oligomerization catalyst is prepared by mixing proportionate volumes of zeolite and alumina to achieve the desired zeolite-to-alumina ratio. In an embodiment, the MTT content may about 5 to 85, for example about 20 to 82 wt % MTT zeolite, and the balance alumina powder will provide a suitably supported catalyst. A silica support is also contemplated.

Monoprotic acid such as nitric acid or formic acid may be added to the mixture in aqueous solution to peptize the alumina in the binder. Additional water may be added to the mixture to provide sufficient wetness to constitute a dough with sufficient consistency to be extruded or spray dried. Extrusion aids such as cellulose ether powders can also be added. A preferred extrusion aid is available from The Dow Chemical Company under the trademark Methocel.

The paste or dough may be prepared in the form of shaped particulates, with the preferred method being to extrude the dough through a die having openings therein of desired size and shape, after which the extruded matter is broken into extrudates of desired length and dried. A further step of calcination may be employed to give added strength to the extrudate. Generally, calcination is conducted in a stream of air at a temperature from about 260° C. (500° F.) to about 815° C. (1500° F.). The MTT catalyst is not selectivated to neutralize acid sites such as with an amine.

The extruded particles may have any suitable cross-sectional shape, i.e., symmetrical or asymmetrical, but most often have a symmetrical cross-sectional shape, preferably a spherical, cylindrical or polylobal shape. The cross-sectional diameter of the particles may be as small as 40 μm; however, it is usually about 0.635 mm (0.25 inch) to about 12.7 mm (0.5 inch), preferably about 0.79 mm (1/32 inch) to about 6.35 mm (0.25 inch), and most preferably about 0.06 mm (1/24 inch) to about 4.23 mm (1/6 inch).

With regard to the oligomerization reactor 1 in FIG. 1, process conditions are optimized to produce a higher percentage of jet range hydrocarbon olefins which, when hydrogenated in subsequent steps as will be described below, result in a desirable jet-range hydrocarbon product. In one exemplary embodiment, an MTT-type zeolite catalyst disposed on a high purity pseudo boehmite alumina substrate in a ratio of about 80/20 is provided within the oligomerization reactor 1 in FIG. 1. The C4 olefins stream 100 are mixed with the C8-olefins from stream 106 to form a mixture of C4 olefins and C8-olefins in stream 101, and the mixture is provided to the oligomerization reactor 1. To achieve the most desirable olefin product, the oligomerization reactor 1 is run at a temperature from about 100° C. to about 230° C., and more preferably from about 111° C. to about 197° C. The oligomerization reactor 1 is run at a pressure from about 300 psig to about 1000 psig, and more preferably from about 710 psig to about 1000 psig.

When the oligomerization reaction is performed according to the above-noted process conditions, a $C_4$ olefin conversion of greater than or equal to about 95% is achieved, or greater than or equal to 97%. The resulting product stream 102 includes a plurality of olefin products that are jet range hydrocarbons.

The effluent from reactor 1 is conveyed to a distillation column 3 via stream 102 where the oligomers that boil lighter than the jet range hydrocarbons, typically $C_8$-components with boiling points <~150° C., are separated from the jet-range hydrocarbons. The jet-range hydrocarbons are then sent for further downstream processing (typically hydrogenation of the olefin) via stream 104 while at least a portion of the $C_8$-components are recycled back to combine with the $C_4$ olefin feedstock in stream 100 via streams 103 and 106. Some of the $C_8$-components can also be purged from the recycle stream via streams 103 and 105.

Figure 2:
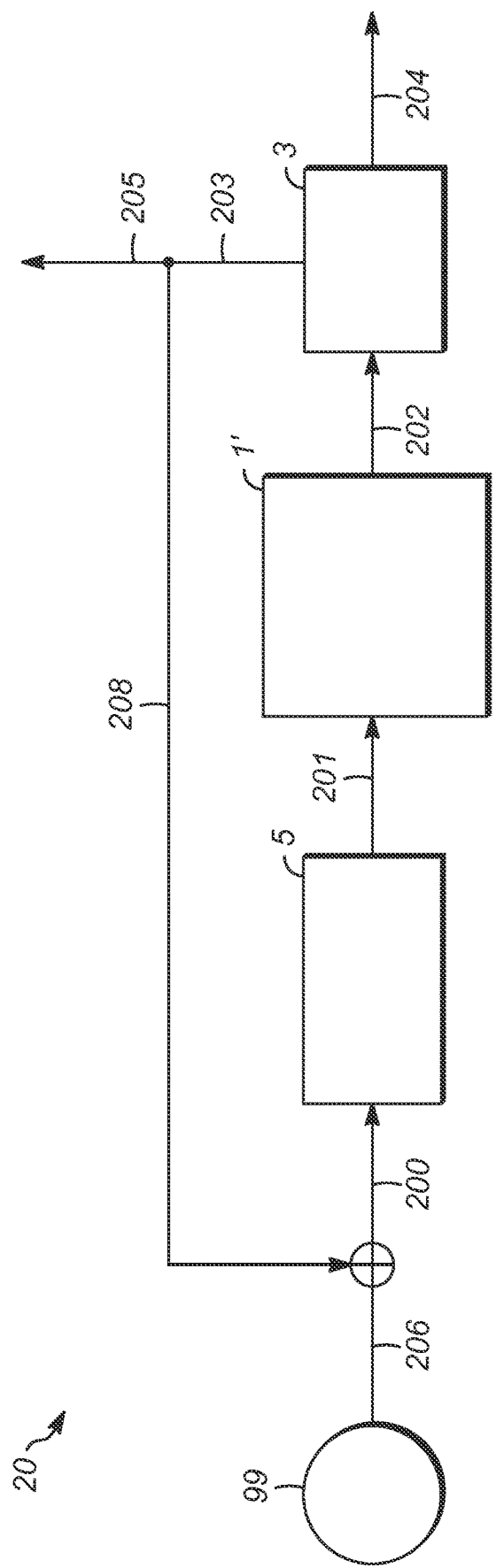
FIG. 2 schematically illustrates another exemplary embodiment of a system utilizing a process for producing jet-range hydrocarbons from biorenewable feedstocks.

FIG. 2 describes another embodiment of a system 20 utilizing an exemplary method for producing jet-range hydrocarbons from a mixture of olefins that includes at least $C_4$ olefins. In this embodiment, feedstock 99 is the same as described above with regard to FIG. 1, and includes at least $C_4$ olefins, which are fed via stream 206 and 200 to dimerization reactor 5. Catalysts used in dimerization reactor 5 are selected for their utility in producing single addition dimers. Preferred dimerization catalysts include sulfonated polystyrene, solid phosphoric acid and other non-crystalline acidic catalysts. The effluent of reactor 5 including dimers of the $C_4$ olefins ($C_8$ olefins) is passed to reactor 1' via stream 201. In the oligomerization reactor 1', at least a portion of the $C_8$ olefins are converted into a mixture of heavier boiling hydrocarbons including jet range hydrocarbons via oligomerization by reacting the $C_8$ olefins using a zeolitic oligomerization catalyst as described previously. Under appropriate reaction conditions, zeolitic catalysts such as MTT, TON, MFI and MTW will yield jet-range hydrocarbons with a broader distribution of components than do non-zeolitic catalysts, such as sulfonated polystyrene resins or solid phosphoric acid catalysts. The increase in the distribution and variety of carbon numbers made by using zeolitic catalysts as compared to a non-zeolitic catalyst is shown above in Table 1. As shown in Table 1, the zeolitic oligomerization reactor selectively converts $C_8$ olefins or mixtures of $C_4$ and $C_8$ olefins to a variety of jet range hydrocarbons.

In currently known methods of producing jet-range hydrocarbons, isobutene oligomerization reactions are performed under conditions so as to optimize the production of $C_{12}$ and $C_{16}$ compounds, i.e. the trimers and tetramers of isobutene. However, as noted above, these methods result in a product with a boiling point distribution that has well-defined boiling point steps corresponding to the $C_{12}$ and $C_{16}$ compounds, which does not resemble regular petroleum-derived jet fuel. In these methods, $C_8$ production is minimized, and any fraction thereof that is formed is removed from the product stream to be used in the production of other chemicals, or further dimerized to form additional $C_{16}$ compounds. As such, in these methods, $C_8$ is viewed as an undesirable byproduct of the isobutene oligomerization reaction.

According to the exemplary methods disclosed herein, in contrast, production of $C_8$ compounds, i.e. the dimers of isobutene, are favored, as $C_8$ compounds exhibit desirable reactivity in a subsequent oligomerization procedure as will be described in greater detail below. As such, in accordance with the exemplary methods herein, the process conditions within reactor 5 in FIG. 2 are optimized for the production of $C_4$ dimers. In one embodiment, an acidic ion exchange resin catalyst is selected for use as the oligomerization catalyst in oligomerization reactor 5. Formulations for acidic ion exchange resin catalysts are well known. For example, some acidic ion exchange resin catalysts that may be used in the disclosed process include, but are not limited to Amberlyst 35, Amberlyst 36, Amberlyst 15, Amberlyst 131 (Rohm and Haas, Woodridge, Ill.), Lewatit S2328, Lewatit K2431, Lewatit S2568, Lewatit K2629 (Sybron Corp, Birmingham, N.J.), Dianion SK104, Dianion PK228, Dianion RCP160, RCP21H, Relite RAD/F (Mitsubishi Chemical, White Plains, N.Y.), and Dowex 50WX4 (Dow Chemical). In an exemplary embodiment, Amberlyst 36 is the preferred catalyst.

Using these catalysts, a desirable production of $C_4$ dimers is achieved by operating the first dimerization reactor 5 at a temperature from about 93° C. to about 120° C., and at a pressure of about 1000 psig. According to these process conditions, selectivity of the $C_8$ isobutene dimer is achieved at greater than or equal to about 40%. The jet range hydrocarbons centered around $C_{12}$ boiling oligomers make up about 40% of the reaction product, and the $C_{16}$ boiling range oligomers make up about 5% of the reaction product. Overall oligomerization conversion according to these process conditions exceeds about 95%.

Suitable catalysts for the functionality of oligomerizing $C_4$ olefin dimers and $C_4$ olefins include various types of zeolite catalysts, in particular MTT-type zeolite catalysts disposed on alumina substrates. In one example, a suitable oligomerization catalyst includes an MTT catalyst comprising a MTT-type zeolite extruded with an alumina binder (high purity pseudo-boehmite CAS Number: 8006-30-2. In another example, a suitable oligomerization catalyst includes an MTT-type zeolite catalyst disposed on alumina substrate (Boehmite alumina) in a range of about 5 to 85, for example about 20 to 82 wt % MTT zeolite, and the balance alumina powder will provide a suitably supported catalyst. In this manner, all oligomerization can be performed in a single process step and using a single catalyst.

In this process step, as with the previous process steps described above, reactor conditions can be optimized to produce the most desirable product composition. With regard to the oligomerization reactor 1' in FIG. 2, process conditions are optimized to produce a higher percentage of jet range hydrocarbon olefins which, when hydrogenated in subsequent steps as will be described below, result in a desirable jet-range hydrocarbon product. In one exemplary embodiment, an MTT-type zeolite catalyst disposed on a high purity pseudo boehmite alumina substrate in a ratio of about 80/20 is provided within the oligomerization reactor 1' in FIG. 2. The $C_4$ dimers are provided to the oligomerization reactor 1' in a feed stream 201. To achieve the most desirable olefin product, the oligomerization reactor 1' is run at a temperature from about 100° C. to about 230° C., and more preferably from about 111° C. to about 197° C. The oligomerization reactor 1' is run at a pressure from about 300 psig to about 1000 psig, and more preferably from about 710 psig to about 1000 psig.

When the oligomerization reaction is performed according to the above-noted process conditions, a $C_4$ dimer conversion of greater than or equal to about 40% is achieved, more typically greater than or equal to about 70%, and most typically greater than or equal to about 80%. The resulting product stream 202 includes a plurality of olefin products that are jet range hydrocarbons.

In some embodiments, it is desirable to hydrogenate product stream 104 in FIG. 1 or product stream 204 in FIG. 2 of jet-range olefins to saturate the olefinic bonds thereof in a hydrogenation reactor. This step is performed to ensure the product jet fuel meets or exceeds the thermal oxidation requirements specified in ASTM D7566-10a for hydroprocessed synthesized paraffinic kerosene (SPK). Hydrogenation is typically performed using a conventional hydrogenation or hydrotreating catalyst, and can include metallic catalysts containing, e.g., palladium, rhodium, nickel, ruthenium, platinum, rhenium, cobalt, molybdenum, or combinations thereof, and the supported versions thereof. Catalyst supports can be any solid, inert substance including, but not limited to, oxides such as silica, alumina, titania, calcium carbonate, barium sulfate, and carbons. The catalyst support can be in the form of powder, granules, pellets, or the like. A stream of $H_2$ is provided as the feed source for hydrogen in the hydrogenation reactor.

In an exemplary embodiment, hydrogenation is performed in a hydrogenation reactor that includes a platinum-on-alumina catalyst, for example 0.7 wt. % platinum-on-alumina catalyst. Using this catalyst, hydrogenation suitably occurs at a temperature of about 150° C. and at a pressure of about 1000 psig. According to these process conditions, the hydrogenation reactor converts the olefins into a paraffin product having the same carbon number distribution as the olefins, thereby forming jet-range paraffins suitable for use as jet fuel. Accordingly, FIGS. 1 and 2 illustrate exemplary systems 10, 20 utilizing a process for producing jet-range hydrocarbons from biorenewable and petroleum feedstocks.

Furthermore, streams 203, 205 function as described above with regard to streams 103, 105 in FIG. 1. Additionally, streams 203, 208 function as described above with regard to streams 103, 106 in FIG. 1. The reaction conditions of reactor 1 described above are suitable for use in both the systems 10, 20. Additionally, fractionation column 3, described above with regard to FIG. 1, functions in substantially the same manner in system 20 as described above with regard to system 10.

Using these systems, for example, a method can be performed for producing jet-range hydrocarbons. It will therefore be appreciated that the foregoing description provides embodiments of a method for producing jet-range hydrocarbons from biorenewable and petroleum feedstocks. The jet-range hydrocarbons produced by the exemplary methods described herein do not suffer from the well-defined boiling point steps observed in other olefin oligomerization-derived jet-range hydrocarbon products produced using catalysts other than MTT, MTW and MFI, and TON. Rather, the jet-range hydrocarbons produced by the exemplary methods described herein include greater variation in the boiling point of its constituent compounds, resulting in a smooth boiling point distribution that more closely resembles petroleum-derived jet-range fuels distilled directly from petroleum crude oil. In this manner, the jet-range hydrocarbons produced by the exemplary methods are anticipated to find greater acceptance and use in the aviation industry.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method for producing jet-range hydrocarbons comprising:
    dimerizing a stream comprising $C_4$ olefins to $C_4$ olefin oligomers over SPA or acidic ion exchange resin catalysts in a dimerization zone to provide a dimerized effluent, wherein conversion of $C_4$ olefins in the dimerizing step is greater than or equal to about 90% and wherein the dimerization zone is operated to favor $C_8$ compounds;
    oligomerizing the entire dimerized effluent over a catalyst consisting of a MTT zeolite on a binder in an oligomerization reactor operated at a temperature of 171 to 197° C. and a pressure of 710 to 890 psig to produce an oligomerized effluent;
    separating the oligomerized effluent to produce a jet range hydrocarbon stream and a recycle stream comprising $C_8$ olefins; and
    passing at least a portion of the recycle stream to the oligomerization reactor,
    wherein a first at least about 10 wt % of the jet-range hydrocarbon stream hydrocarbons have boiling points between the boiling point of n-octane and the boiling point of n-undecane and wherein a second at least about 10 wt % of the jet-range hydrocarbon stream hydrocarbons have boiling points between the boiling point of n-dodecane and the boiling point of n-pentadecane.

2. The method of claim 1, wherein the $C_4$ olefins are derived from dehydrating a renewable alcohol with a $^{14}C/^{12}C$ ratio indicative of atmospheric carbon.

3. The method of claim 1, wherein the dimerization zone operates at a temperature from about 93° C. to about 120° C. and a pressure of about 1000 psig to produce $C_4$ olefin oligomers.

4. The method of claim 1, wherein the binder comprises alumina powder and wherein in the combined MTT zeolite and alumina powder, the MTT zeolite is present in an amount of from about 5 to about 85 wt % MTT with the balance alumina powder.

5. The method of claim 4, wherein in the combined MTT zeolite and alumina powder the MTT zeolite is present in an amount of from about 20 to about 82 wt % MTT with the balance being the alumina powder.

6. The method of claim 1, further comprising hydrogenating the jet range hydrocarbon stream in a hydrogenation reactor.

7. A method for producing jet-range hydrocarbons comprising:
- dimerizing a stream comprising $C_4$ olefins to $C_4$ olefin oligomers over SPA or acidic ion exchange resin catalysts in a dimerization zone to provide a dimerized effluent, wherein conversion of $C_4$ olefins in the dimerizing step is greater than or equal to about 90% and wherein the dimerization zone is operated to favor $C_8$ compounds;
- oligomerizing the dimerized effluent over a catalyst consisting of a MTT zeolite on a binder in an oligomerization reactor operated at a temperature of 171 to 197° C., a liquid hourly space velocity of about 0.75 to 1.50 $hr^{-1}$ and a pressure of 710 to 890 psig to produce an oligomerized effluent, wherein a first at least about 10 wt.-% of the oligomerized effluent hydrocarbons have boiling points between the boiling point of n-octane and the boiling point of n-undecane and wherein a second at least about 10 wt.-% of the oligomerized effluent hydrocarbons have boiling points between the boiling point of n-dodecane and the boiling point of n-pentadecane;
- separating the oligomerized effluent by distillation to produce a jet range hydrocarbon stream and a recycle stream comprising $C_8$ olefins; and
- passing at least a portion of the recycle stream to the dimerization zone, wherein the jet-range hydrocarbons comprise between 14 and 16 wt % $C_{16}$ hydrocarbons.

8. The method of claim 7, wherein the $C_4$ olefins are derived from dehydrating a renewable alcohol with a $^{14}C/^{12}C$ ratio indicative of atmospheric carbon.

9. The method of claim 7, wherein the binder comprises alumina powder and wherein in the combined MTT zeolite and alumina powder, the MTT zeolite is present in an amount of from about 5 to about 85 wt % MTT with the balance alumina powder.

10. The method of claim 7, wherein the binder comprises alumina powder and wherein in the combined MTT zeolite and alumina powder, the MTT zeolite is present in an amount of from about 20 to about 82 wt % MTT with the balance alumina powder.

11. The method of claim 7, further comprising hydrogenating the jet range hydrocarbon stream in a hydrogenation reactor.

12. A method for producing jet-range hydrocarbons comprising:
- dimerizing $C_4$ olefins over SPA or acidic ion exchange resin catalysts in a dimerization zone to produce dimers of the $C_4$ olefins, wherein conversion of the $C_4$ olefins in the dimerizing step is greater than or equal to about 90% and wherein the dimerization zone is operated to favor $C_8$ compounds;
- oligomerizing a stream comprising the dimers of the $C_4$ olefins over a catalyst consisting of a MTT zeolite on a binder in an oligomerization reactor to produce an oligomerized effluent, wherein a first at least about 10 wt.-% of the oligomerized effluent hydrocarbons have boiling points between the boiling point of n-octane and the boiling point of n-undecane and wherein a second at least about 10 wt.-% of the oligomerized effluent hydrocarbons having boiling points between the boiling point of n-dodecane and the boiling point of n-pentadecane;
- separating the oligomerized effluent by distillation to produce a jet range hydrocarbon stream and a recycle stream comprising $C_8$ olefins; and
- passing at least a portion of the recycle stream to the dimerization zone.

* * * * *